United States Patent
Chiou et al.

(10) Patent No.: US 9,504,751 B2
(45) Date of Patent: Nov. 29, 2016

(54) STABLE PHARMACEUTICAL COMPOSITION

(71) Applicant: EVERFRONT BIOTECH INC., New Taipei (TW)

(72) Inventors: Tzyy-Wen Chiou, New Taipei (TW); Horng-Jyh Harn, New Taipei (TW); Shinn-Zong Lin, New Taipei (TW); Yu-Han Chiu, New Taipei (TW)

(73) Assignee: EVERFRONT BIOTECH INC., New Taipei (TW)

( * ) Notice: Subject to any disclaimer, the term of this patent is extended or adjusted under 35 U.S.C. 154(b) by 57 days.

(21) Appl. No.: 14/695,088

(22) Filed: Apr. 24, 2015

(65) Prior Publication Data

US 2015/0306233 A1    Oct. 29, 2015

Related U.S. Application Data

(60) Provisional application No. 61/983,619, filed on Apr. 24, 2014, provisional application No. 62/023,205, filed on Jul. 11, 2014.

(30) Foreign Application Priority Data

Apr. 15, 2015   (TW) .............................. 104112055 A

(51) Int. Cl.
| | |
|---|---|
| *A61K 31/365* | (2006.01) |
| *A61K 47/44* | (2006.01) |
| *A61K 31/343* | (2006.01) |
| *A61K 47/02* | (2006.01) |
| *A61K 47/10* | (2006.01) |
| *A61K 47/20* | (2006.01) |
| *A61K 9/00* | (2006.01) |
| *A61K 9/107* | (2006.01) |

(52) U.S. Cl.
CPC ............ *A61K 47/44* (2013.01); *A61K 9/1075* (2013.01); *A61K 31/343* (2013.01); *A61K 31/365* (2013.01); *A61K 47/02* (2013.01); *A61K 47/10* (2013.01); *A61K 47/20* (2013.01); *A61K 9/0043* (2013.01); *A61K 9/107* (2013.01)

(58) Field of Classification Search
USPC ........................................ 514/449, 469, 470
See application file for complete search history.

(56) References Cited

U.S. PATENT DOCUMENTS

| | | |
|---|---|---|
| 2006/0110469 A1 | 5/2006 | Luo et al. |
| 2008/0319056 A1 | 12/2008 | Liu et al. |
| 2009/0281177 A1 | 11/2009 | Zhao et al. |
| 2012/0208875 A1* | 8/2012 | Lin ..................... A61K 31/365 514/470 |

OTHER PUBLICATIONS

Pharmaceutical solutions for oral administration (Chapter 1; Jul. 5, 2008, pp. 1-24).*

* cited by examiner

*Primary Examiner* — Pancham Bakshi
(74) *Attorney, Agent, or Firm* — McClure, Qualey & Rodack, LLP

(57) ABSTRACT

A pharmaceutical composition comprising:
(a) a medium system, comprising a first component, a second component and a third component, wherein the first component is a phosphate buffered saline, the second component is selected from the group consisting of vegetable oils, animal oils, fatty acids and combinations thereof, and the third component is selected from the group consisting of polyethylene glycol, dimethyl sulfoxide (DMSO), ethanol, polypropylene glycol, polysorbate, polyoxyethylated vegetable oil, ethyl acetate, 2-hydroxyethyl 12-hydroxyoctadecanoate, tocopheryl polyethylene glycol succinate and combinations thereof; and
(b) n-butylidenephthalide (BP).

13 Claims, 11 Drawing Sheets
(8 of 11 Drawing Sheet(s) Filed in Color)

(A) Untreated (obtained after rats died)
(B) Pure BP 160 mg/kg (day 37)
(C) Pure BP 320 mg/kg (day 37)
(D) Pharmaceutical composition 5 80 mg/kg (day 37)
(E) Pharmaceutical composition 5 160 mg/kg (day 37)

STABLE PHARMACEUTICAL COMPOSITION

CLAIM FOR PRIORITY

This application claims the benefits of U.S. Provisional Patent Application No. 61/983,619, filed on Apr. 24, 2014 and U.S. Provisional Patent Application No. 62/023,205, filed on Jul. 11, 2014. This application also claims priority to Taiwan patent application No. 104112055, filed Apr. 15, 2015. The contents of these priority applications are incorporated herein by reference.

CROSS-REFERENCES TO RELATED APPLICATIONS

Not applicable.

BACKGROUND OF THE INVENTION

Field of the Invention

The present invention relates to a pharmaceutical composition comprising a medium system and n-butylidenephthalide which is stable in the medium system. Particularly, the present invention relates to a pharmaceutical composition with n-butylidenephthalide that can be administrated by intranasal administration and is effective in the treatment of malignant brain tumor.

Descriptions of the Related Art

Astrocyroma, anaplastic astrocytoma and glioblastoma multiforme (GBM) are common malignant brain tumors of adults, among them, glioblastoma multiforme is the most common, most malignant and most invasive one.

Malignant brain tumor is a highly invasive disease with a very high death rate. The effective treatment method for this disease is still an unmet medical need. Currently there are three types of treatment, i.e., surgery, radiotherapy and chemotherapy. Surgery can eliminate most of the tumor, but it will hurt the other normal brain tissue and thereby affect the patient's athletic ability and linguistic ability. Radiotherapy can partially eliminate the tumor, but also affect the surrounding normal tissue cells. Chemotherapy usually fails to provide a significant therapeutic effect because of the blood-brain barrier (BBB) problem, significant toxic side effects and drug resistance. Intranasal administration is a new and non-invasive administration route and therefore can reduce the risk of infection. Once a drug being administrated via nasal cavity, it can be rapidly absorbed through the nasal mucosa to generate desired efficacy without being affected by the liver first-pass metabolism. Furthermore, the drug absorbed through the nasal mucosa can easily pass through the blood-brain barrier and directly reach the central nervous system, and thus the toxicity effect can be reduced.

N-butylidenephthalide (BP) is a potential new drug for the treatment of malignant tumors, which is derived from the extract of *Angelica sinensis*. N-butylidenephthalide has a boiling point of 139° C. to 142° C. (5 mmHg) and thus is oil like under normal conditions. It is known that n-butylidenephthalide is effective in the treatment of various cancers including glioblastoma multiforme and mammary cancer. Furthermore, latest researches reveal that n-butylidenephthalide is effective in inhibiting the autophagy of motor neurons. For instance, US 2014/0045765 A1 discloses that n-butylidenephthalide and its metabolic products are effective in inhibiting the autophagy of motor neurons and can be used for used for curing amyotrophic lateral sclerosis (ALS).

Unfortunately, BP is hydrophobic compound and not soluble in water. Such a hydrophobic feature of n-butylidenephthalide strictly limits its uses as a formulation for oral administration, injection and/or intranasal administration, and restricts its clinical applications and animal studies wherein light animals such as rats are used in the studies.

Therefore, a dosage form of n-butylidenephthalide in which n-butylidenephthalide is soluble or stable is desired in the art so as to enhance the bioavailability of n-butylidenephthalide and to facilitate the transportation and/or delivery as well as the pre-clinical researches of n-butylidenephthalide. The present invention is an achievement developed in view of the above needs, which applies a medium system to stabilize n-butylidenephthalide and enhance its efficacy.

SUMMARY OF THE INVENTION

An objective of the present invention is to provide a pharmaceutical composition comprising (a) a medium system, comprising a first ingredient, a second ingredient and a third ingredient, wherein the first ingredient is a phosphate buffered saline, the second ingredient is selected from the group consisting of vegetable oils, animal oils, fatty acids and combinations thereof, and the third ingredient is selected from the group consisting of polyethylene glycol, dimethyl sulfoxide (DMSO), ethanol, polypropylene glycol, polysorbate, polyoxyethylated vegetable oil, ethyl acetate, 2-hydroxyethyl 12-hydroxyoctadecanoate, tocopheryl polyethylene glycol succinate and combinations thereof; and (b) n-butylidenephthalide (BP).

The detailed technology and preferred embodiments implemented for the present invention are described in the following paragraphs accompanying the appended drawings for persons with ordinary skill in the art to well appreciate the features of the claimed invention.

BRIEF DESCRIPTION OF THE DRAWINGS

The patent application contains at least one drawing executed in color. Copies of this patent document with color drawing(s) will be provided by the Office upon request and payment of the necessary fee.

DESCRIPTION OF THE PREFERRED EMBODIMENT

Figure 1A:
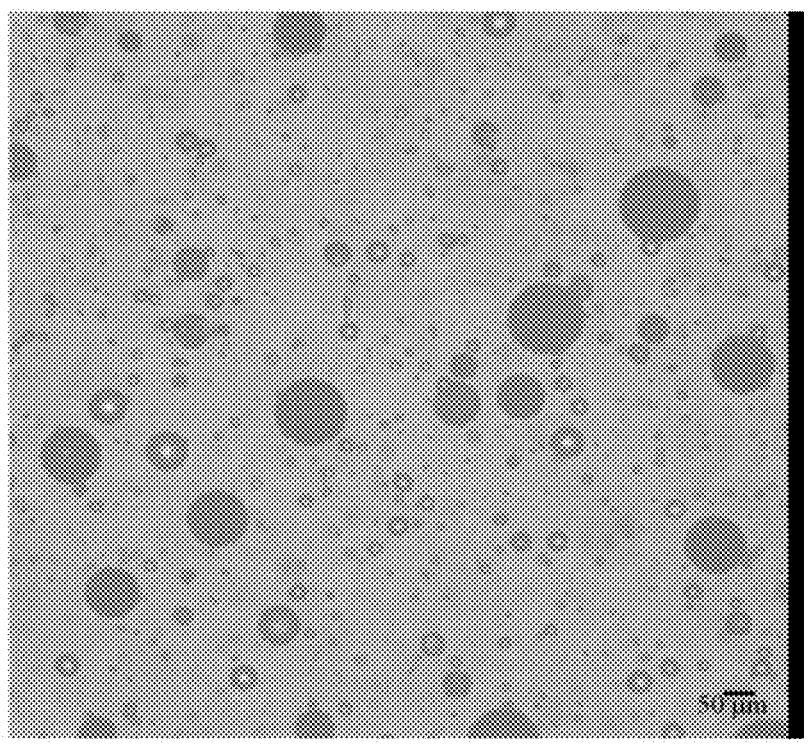
FIG. 1A shows the inverted microscope (1M) image (400×; bar: 50 μm) of an embodiment of the pharmaceutical composition according to the present invention.

The following will describe some embodiments of the present invention in detail. However, without departing from the spirit of the invention, the present invention may be embodied in various embodiments and should not be limited to the embodiments described in the specification. In addition, unless otherwise stated herein, the terms "a (an)", "the", or the like used in this specification (especially in the claims hereinafter) shall be understood to encompass both the singular and plural forms.

It is known that an active ingredient with therapeutic effect is normally administered in a liquid dosage form which comprises the active ingredient and a medium in which the active ingredient is soluble or stable. Specifically, in accordance with the administration type (e.g., oral administration, introduction into body cavities or external use), the active ingredient may be dissolved in the medium (if it is soluble) or is suspended in the medium (if it is insoluble) so as to provide a solution, suspension or emulsion suitable for administration. Furthermore, for preparing a solid dosage form containing a small amount of an active ingredient, the active ingredient is normally dissolved or suspended in a liquid medium and then the liquid medium is used for the preparation so as to precisely control the concentration (or amount) of the active ingredient in the final product.

The inventors discovered through researches that ethanol is an excellent solvent for n-butylidenephthalide because of the highest solubility of n-butylidenephthalide. For instance, the solubility of n-butylidenephthalide in ethanol is more than 222 mg/mL while that in polyethylene glycol 400, polyethylene glycol 300 or polypropylene glycol was about 70 to 120 mg/mL. However, previous studies reveal that neonates and infants are not able to metabolise ethanol as efficiently as adults since they have immature alcohol dehydrogenase (see such as Zuccotti G V, Fabiano V. Safety issues with ethanol as an excipient in drugs intended for pediatric use. Expert Opin Drug Saf 2011; 10(4):499-502, which is incorporated by reference in its entirety). Therefore, the scope of n-butylidenephthalide will be greatly widened if the ethanol can be replaced by other solvent(s) from the medium of n-butylidenephthalide or its content in the medium can be lowered as much as possible.

The inventors conducted further researches and discovered that n-butylidenephthalide is stable in a particular medium system. In this medium system, n-butylidenephthalide is stable while its activity is maintained even after a long-term storage (3 days at room temperature, or 30 days at 4° C.). Moreover, the medium system could further improve the bioavailability of n-butylidenephthalide such that the desired therapeutic effect can be obtained with a lower dosage of n-butylidenephthalide and the side effects can be alleviated or avoided accordingly.

Therefore, the present invention relates to a stable pharmaceutical composition, which comprises (a) a medium system and (b) n-butylidenephthalide stable in the medium system (a).

N-butylidenephthalid is commercially available (for example, could be purchased from ECHO CHEMICAL CO., LTD, TW), and can be produced through chemical synthesis or extracted from natural materials (e.g., *Angelica sinensis*). N-butylidenephthalide provided by extraction can be further purified by techniques such as flash column chromatography, high performance liquid chromatography or crystallization method prior to being used.

According to the present invention, the medium system (a) comprises a first ingredient, a second ingredient and a third ingredient, wherein the first ingredient is a phosphate buffered saline, the second ingredient is selected from the group consisting of vegetable oils, animal oils, fatty acids and combinations thereof, and the third ingredient is selected from the group consisting of polyethylene glycol, dimethyl sulfoxide (DMSO), ethanol, polypropylene glycol, polysorbate, polyoxyethylated vegetable oil, ethyl acetate, 2-hydroxyethyl 12-hydroxyoctadecanoate, tocopheryl polyethylene glycol succinate and combinations thereof.

Phosphate buffered saline as the first ingredient of the medium system (a) is isotonic and non-toxic to cells. Any suitable phosphate buffered saline can be used in the present invention. Examples of phosphate buffered saline include, but are not limited to, a combination of NaCl (137 mM) and KCl (2.7 mM) in water, and a combination of $Na_2HPO_4$ (10 mM), $KH_2PO_4$ (1.8 mM), NaCl (137 mM) and KCl (2.7 mM) in water.

With regard to the second ingredient of the medium system (a), examples of vegetable oils include, but are not limited to, one or more selected from canola oil, coconut oil, corn oil, cotton seed oil, olive oil, palm oil, peanut oil, rape seed oil, safflower seed oil, sesame oil, bean oil, heliotrope oil, almond oil, cashewnut oil, hazelnut oil, walnut oil, hickory nut oil, pine nut oil, pistachio oil and castor oil; and examples of animal oils include, but are not limited to, one or more selected from fish oil, fish liver oil, lard oil, tallow oil, caproin, chicken oil and duck oil; and the fatty acids may be saturated fatty acids or unsaturated fatty acids (e.g., cis-unsaturated fatty acids, monounsaturated fatty acids, polyunsaturated fatty acids and trans-unsaturated fatty acids). In some embodiments of the present invention, the second ingredient is a modified castor oil. Examples of the modified castor oil include, but are not limited to, polyethoxylated castor oil and hydrogenated, polyethoxylated castor oil. Polyethoxylated castor oil is also known as glycerol polyethyleneglycol ricinoleate, as marketed, e.g., under the name Kolliphor® EL (former name: Cremophor® EL; from BASF). Kolliphor® EL is a non-ionic solubilizer and emulsifier that can be obtained by reacting ethylene oxide with castor oil. Hydrogenated, ethoxylated castor oils can be obtained by reacting ethylene oxide with hydrogenated castor oil. Examples of hydrogenated, ethoxylated castor oils include, but are not limited, polyoxyl 40 hydrogenated castor oil and polyoxyl 60 hydrogenated castor oil, wherein the former is commercially available under the name such as Kolliphor® RH 40 (HLB=14-16) from BASF and the latter is commercially available under the name such as Kolliphor® RH 60 (HLB=15-17) from BASF.

With regard to the third ingredient of the medium system (a), polysorbate is marketed under the name "Tween." Examples of polysorbate suitable for the present invention include, but are not limited to, polysorbate 20, polysorbate 80 and polysorbate 85. Polyoxyethylated vegetable oil, is marketed under the name "Emulphor." 2-hydroxyethyl 12-hydroxyoctadecanoate is commercially available under the name such as Kolliphor® HS 15 (also named Solutol® HS 15) from BASF. Examples of tocopheryl polyethylene glycol succinate (TPGS) suitable for the present invention include, but are not limited to, D-α-Tocopherol polyethylene glycol 1000 succinate (HLB=13.2). However, the third ingredient of the medium system (a) are not limited to the above examples.

In some embodiments of the present invention, the medium system (a) is a mixture consisting of phosphate buffered saline (first ingredient), polyethoxylated castor oil (second ingredient) and a component (third ingredient) selected from the group consisting of polyethylene glycol, dimethyl sulfoxide, ethanol, polypropylene glycol and combinations thereof. Among them, n-butylidenephthalide is much more stable in the medium system that the third ingredient is selected from polyethylene glycol, dimethyl sulfoxide and ethanol, so that the pharmaceutical composition can be stored for a long time without separating into two layers and the activity of n-butylidenephthalide can be maintained. In particular, the efficacy of the pharmaceutical composition of the present invention is better in the case that the third ingredient is a combination of polyethylene glycol and dimethyl sulfoxide or a combination of polyethylene glycol and ethanol, especially in the case that the third ingredient is a combination of polyethylene glycol and dimethyl sulfoxide. Therefore, in the medium system (a) of the pharmaceutical composition of the present invention, the third ingredient is preferably selected from the group consisting of polyethylene glycol, dimethyl sulfoxide, ethanol and combinations thereof, and more preferably a combination of polyethylene glycol and dimethyl sulfoxide or a combination of polyethylene glycol, especially a combination of polyethylene glycol and dimethyl sulfoxide.

According to the present invention, the concentration of the constituent (b), i.e., n-butylidenephthalide, is not particularly limited as long as the n-butylidenephthalide is stable in the medium system (a). Accordingly, in the case that n-butylidenephthalide is dissolved in the medium system (a), the amount of n-butylidenephthalide is typically not higher than its solubility in said medium system (a); and in the case that n-butylidenephthalide is suspended in the medium system (a), the amount of n-butylidenephthalide is typically controlled in such a way that the pharmaceutical composition will not separate into layers. In accordance with these principles, in some embodiments of the present invention, n-butylidenephthalide is in an amount of 0.001 mg to 1500 mg per milliliter (mL) of the medium system.

For example, as illustrated in the appended Examples, when the medium system (a) is provided using phosphate buffered saline ([$Na_2HPO_4$]=10 mM, [$KH_2PO_4$]=1.8 mM, [NaCl]=137 mM and [KCl]=2.7 mM) as the first ingredient, polyethoxylated castor oil as the second ingredient, and a combination of polyethylene glycol and dimethyl sulfoxide or a combination of polyethylene glycol and ethanol as the third ingredient (see Examples 1, 5 and 6), constituent (b) (n-butylidenephthalide) is stable in the medium system in an amount up to 1000 mg/mL. This result indicates that the amount of n-butylidenephthalide in the provided pharmaceutical composition can be at least 1000 mg per 1 mL of the medium system. Furthermore, when the medium system (a) is provided using phosphate buffered saline ([$Na_2HPO_4$]=10 mM, [$KH_2PO_4$]=1.8 mM, [NaCl]=137 mM and [KCl]=2.7 mM) as the first ingredient, polyethoxylated castor oil as the second ingredient, and a combination of ethanol and polypropylene glycol (PPG) as the third ingredient, constituent (b) (n-butylidenephthalide) can be stable in the medium system in an amount up to 208 mg/mL. This result indicates that the amount of n-butylidenephthalide in the provided pharmaceutical composition can be at least 208 mg per mL of the medium system.

Among the medium system (a) of the pharmaceutical composition of the present invention, the ratio of the ingredients can be selected and adjusted by persons skilled in the art depending on the combination of selected ingredients based the disclosure provided in this text. For instance, the volume ratio of the first ingredient to the second ingredient may be from 1:2 to 20:1, such as 1:1, 2:1. 3:1, 4:1, 5:1, 8:1, 10:1, 13:1, 15:1, 17:1 and 20:1; and the volume ratio of the first ingredient to the third ingredient may be from 1:2 to 30:1, such as 1:1, 2:1. 3:1, 4:1, 5:1, 8:1, 10:1, 13:1, 15:1, 17:1, 20:1, 25:1 and 30:1. In addition, in the case that the third ingredient is a mixture of multiple components, the proportions of the components may be selected by user depending on such as the properties of the components. For example, in the case that the third ingredient is a mixture of ethanol and polyethylene glycol, the volume ratio of ethanol to polyethylene glycol is not particularly limited because ethanol and polyethylene glycol can be evenly mixed in any proportions. The volume ratio of ethanol to polyethylene glycol may be, for example, 10:1 to 1:100, preferably 6:1 to 1:50, more preferably 1:1 to 1:10.

For example, in the case that the medium system (a) is provided using phosphate buffered saline ([$Na_2HPO_4$]=10 mM, [$KH_2PO_4$]=1.8 mM, [NaCl]=137 mM and [KCl]=2.7 mM) as the first ingredient, polyethoxylated castor oil as the second ingredient, and polyethylene glycol as the third ingredient, the volume of phosphate buffered saline to polyethoxylated castor oil may be 3:0.5-5 (e.g., 3:1), and the volume of phosphate buffered saline to polyethylene glycol may be 3:0.55 (e.g., 3:1). In the case that the medium system (a) is provided using phosphate buffered saline as the first ingredient, polyethoxylated castor oil as the second ingredient, and a combination of polyethylene glycol and dimethyl sulfoxide as the third ingredient, the volume of phosphate buffered saline to polyethoxylated castor oil may be 1-10:1 (e.g., 5:1), the volume of phosphate buffered saline to the combination of polyethylene glycol and dimethyl sulfoxide may be 1-5:1 (e.g., 3:1), and the volume of polyethylene glycol to dimethyl sulfoxide may be 1-2:1-2 (e.g., 1:1).

In the pharmaceutical composition of the present invention, constituent (b), n-butylidenephthalide, is soluble or stable in the medium system and thus the composition can be in form as a solution or an emulsion or suspension suitable for the transportation of n-butylidenephthalide or its administration. For instance, the pharmaceutical composition can be administered to a subject in need by oral administration, injection and/or intranasal administration.

Furthermore, since n-butylidenephthalide is soluble or stable in the medium system, the pharmaceutical composition of the present invention facilitates the researches with the use of animal models wherein light animals such as mice of about 25 grams are used. For instance, when mice of about 25 grams are used as the animal model for the research of the effects of n-butylidenephthalide, a tiny amount of such as 2 to 3 µL of n-butylidenephthalide would be used in the studies while it is difficult to meter such a tiny amount. With the use of the pharmaceutical composition of the present invention, since n-butylidenephthalide is stable in the medium system and thus is diluted by the medium system, the desired tiny amount of n-butylidenephthalide can be provided as the pharmaceutical composition in a relatively large volume and thus, the metering will be much more easy and precise. Accordingly, the pharmaceutical composition of the present invention can be used for the preparation of a solid dosage of n-butylidenephthalide to precisely control the concentration (or amount) of n-butylidenephthalide in the final product.

The pharmaceutical composition of the present invention can be prepared by simply mixing the medium system (a) and the constituent (b), n-butylidenephthalide. In the case that n-butylidenephthalide is soluble in the medium system, n-butylidenephthalide is directly added into the medium system so as to be dissolved therein. As for the case that n-butylidenephthalide is not soluble in the medium system, n-butylidenephthalide is added into the medium system with stirring to provide a stable emulsion or suspension with n-butylidenephthalide suspended therein as micro- or nano-droplets.

The pharmaceutical composition of the present invention may further comprise other additives or other active ingredients as long as the additives and said other active ingredients will not adversely influence the effect of n-butylidenephthalide or the stability and/or solubility of n-butylidenephthalide in the medium system. For example, to improve the storability of the pharmaceutical composition of the present invention, the pharmaceutical composition may also comprise a suitable amount of a preservative, a conservative, an antiseptic, an anti-fungus reagent, etc.; and the pharmaceutical composition of the present invention may comprise one or more other active ingredients, such as an antioxidant (e.g., vitamin E, vitamin C, butylated hydroxyanisole, butylated hydroxytoluene), chemotherapy drugs, immune modulators, etc., to further enhance the efficacy of the pharmaceutical composition thus provided or to increase the application flexibility and adaptability of the pharmaceutical composition.

The present invention will be further illustrated in details with specific examples as follows. However, the following examples are provided only for illustrating the present invention, and the scope of the invention is not limited thereby. In the examples, n-butylidenephthalide is metered by volume and converted with a density of 1 g/mL to obtain the corresponding weight.

EXAMPLES

1. Room-Temperature Stability Test

1.1 Testing Method

The stability study of the pharmaceutical composition was performed by: (1) observing the appearance of the pharmaceutical composition after storage at room temperature for 3 or 7 days, and classifying the results into "V" (if the pharmaceutical composition remained homogeneous) and "X" (if the pharmaceutical composition separated into two layers or had precipitation) to evaluate the appearance stability; and (2) analyzing the purity of n-butylidenephthalide by measuring the impurities in the pharmaceutical composition through relative retention time (RRT) using a LCMS instrument with the following conditions.

| | |
|---|---|
| Instrument | Agilent 1260 series |
| Column | PLUS, C8, 100 × 4.6 mm, 3.5 µm |
| Column temperature | 45° C. |
| Mobile phase | A: 0.05% Formic in $H_2O$, B: 0.05% Formic in ACN |
| Gradient condition (% of B) | 0/5%, 8/10%, 12.0/100% |
| Flow rate | 1.5 mL/min |
| Injection volume | 5 µL |
| Sample temperature | 45° C. |
| UV wavelength | 254 nm |

1.2 Preparation of Pharmaceutical Composition

Example 1

According to the ratio shown in Table 1, 50 µL of n-butylidenephthalide (BP) (Everfront Inc., Lot No. F212TR12001), 10 µL of polyethylene glycol (PEG) (SIGMA, Lot No. MKBG2152V, CAS: 25322-68-3) and 10 µL of polyethoxylated castor oil (Kolliphor® EL, hereinafter "K-EL"; SIGMA, Lot No. BCBC54780; CAS:61791-12-6) were mixed to provide a mixture, and then 30 µL of phosphate buffered saline (hereinafter "PBS"; $[Na_2HPO_4]$= 10 mM, $[KH_2PO_4]$=1.8 mM, [NaCl]=137 mM and [KCl]= 2.7 mM) was dropped into the mixture while stirring and an emulsion of pharmaceutical composition 1 was obtained.

Example 2

The preparation procedures of Example 1 were repeated to prepare an emulsion of pharmaceutical composition 2, except that the amounts of the components were adjusted as shown in Table 1.

Example 3

The preparation procedures of Example 1 were repeated to prepare an emulsion of pharmaceutical composition 3, except that dimethyl sulfoxide (DMSO) was used as the third ingredient, and the amounts of the components were adjusted as shown in Table 1.

Example 4

The preparation procedures of Example 1 were repeated to prepare an emulsion of pharmaceutical composition 4, except that the amounts of the components were adjusted as shown in Table 1.

Example 5

The preparation procedures of Example 1 were repeated to prepare an emulsion of pharmaceutical composition 5, except that a combination of PEG and DMSO was used as the third ingredient, and the amounts of the components were adjusted as shown in Table 1.

Example 6

The preparation procedures of Example 1 were repeated to prepare an emulsion of pharmaceutical composition 6, except that a combination of PEG and ethanol was used as the third ingredient, and the amounts of the components were adjusted as shown in Table 1.

Comparative Example 1

The preparation procedures of Example 1 were repeated to prepare an emulsion of comparative pharmaceutical composition 1, except that the second ingredient (K-EL) was not added and a combination of PEG and Kolliphor® HS 15 (hereafter "HS 15"; from BASF; Lot No. 14225516K0; CAS No.: 61909-81-7) was used as the third ingredient as shown in Table 1.

TABLE 1

Proportions (volume %) of components of pharmaceutical compositions

| Pharmaceutical composition | | 1 | 2 | 3 | 4 | 5 | 6 | Comparative 1 |
|---|---|---|---|---|---|---|---|---|
| Active ingredient | BP | 50 | 25 | 1.44 | 0.72 | 50 | 50 | 50 |
| First ingredient | PBS | 30 | 65 | 83.56 | 84.28 | 30.5 | 30.5 | 30 |
| Second ingredient | K-EL | 10 | 5 | 10 | 10 | 6.5 | 6.5 | |
| Third ingredient | PEG | 10 | 5 | | | 6.5 | 6.5 | 10 |
| | DMSO | | | 5 | 5 | 6.5 | | |
| | HS 15 | | | | | | | 10 |
| | Ethanol | | | | | | 6.5 | |

1.3 Results of Room-Temperature Stability Test

The pharmaceutical compositions 1 to 6 and comparative pharmaceutical composition 1 were tested by observing the appearance and measuring the amount of impurities according to the testing method as described in point 1.1 to evaluate stability. The results are tabulated in Table 2, Tables 3-1 to 3-7 and Table 4, wherein Table 2 shows the appearance of the emulsions, Tables 3-1 to 3-7 show the amount of impurities (volume %) in pharmaceutical compositions 1 to 6 and comparative pharmaceutical composition 1 respectively, and Table 4 shows the volume percentage of the active ingredient (BP) maintained in the pharmaceutical compositions after different time periods derived from the data in Tables 3-1 to 3-7.

TABLE 2

Appearance of pharmaceutical composition observed before and after storage at room temperature (RT)

| Pharmaceutical composition | 1 | 2 | 3 | 4 | 5 | 6 | Comparative 1 |
|---|---|---|---|---|---|---|---|
| Initial | V | V | V | V | V | V | V |
| After 3 days at RT | V | V | V | V | V | V | X |
| After 7 days at RT | X | V | V | V | X | X | X |

TABLE 3-1

Amount of impurities (volume %) in the pharmaceutical composition 1 after different time periods

| RRT | RRT 0.7 | RRT 0.86 | RRT 0.89 | RRT 0.9 | Total |
|---|---|---|---|---|---|
| Initial | 0.32 | ND | ND | ND | 0.32 |
| After 3 days at RT | 0.36 | ND | ND | 0.3 | 0.66 |
| After 7 days at RT | 0.43 | 0.25 | 0.08 | 0.84 | 1.60 |

*ND means "not detected."

TABLE 3-2

Amount of impurities (volume %) in the pharmaceutical composition 2 after different time periods

| RRT | RRT 0.7 | RRT 0.86 | RRT 0.89 | RRT 0.9 | Total |
|---|---|---|---|---|---|
| Initial | 0.25 | ND | ND | <0.05 | 0.25 |
| After 3 days at RT | 0.73 | ND | ND | 1.24 | 1.97 |
| After 7 days at RT | 0.43 | 0.23 | 0.10 | 0.71 | 1.47 |

TABLE 3-3

Amount of impurities (volume %) in the pharmaceutical composition 3 after different time periods

| RRT | RRT 0.7 | RRT 0.8 | RRT 0.86 | Total |
|---|---|---|---|---|
| Initial | 0.11 | <0.05 | <0.05 | 0.11 |
| After 3 days at RT | 0.20 | 0.12 | <0.05 | 0.32 |
| After 7 days at RT | 0.42 | 0.15 | 0.11 | 0.68 |

TABLE 3-4

Amount of impurities (volume %) in pharmaceutical composition 4 after different time periods

| RRT | RRT 0.7 | RRT 0.8 | RRT 0.86 | Total |
|---|---|---|---|---|
| Initial | 0.09 | ND | <0.05 | 0.09 |
| After 3 days at RT | 0.11 | 0.11 | <0.05 | 0.22 |
| After 7 days at RT | 0.19 | 0.16 | 0.07 | 0.42 |

TABLE 3-5

Amount of impurities (volume %) in the pharmaceutical composition 5 after different time periods

| RRT | RRT 0.7 | RRT 0.86 | RRT 0.89 | RRT 0.9 | Total |
|---|---|---|---|---|---|
| Initial | 0.04 | 0.01 | 0.07 | 0.02 | 0.14 |
| After 3 days at RT | 0.02 | 0.33 | 0.02 | 0.03 | 0.40 |
| After 7 days at RT | 0.02 | 0.67 | ND | 0.02 | 0.71 |

TABLE 3-6

Amount of impurities (volume %) in the pharmaceutical composition 6 after different time periods

| RRT | RRT 0.7 | RRT 0.86 | RRT 0.89 | RRT 0.9 | Total |
|---|---|---|---|---|---|
| Initial | 0.03 | 0.01 | 0.06 | 0.02 | 0.12 |
| After 3 days at RT | 0.02 | 0.33 | 0.01 | 0.02 | 0.38 |
| After 7 days at RT | 0.02 | 0.57 | ND | 0.02 | 0.61 |

TABLE 3-7

Amount of impurities (volume %) in the comparative pharmaceutical composition 1 after different time periods

| RRT | RRT 0.7 | RRT 0.86 | RRT 0.9 | Total |
|---|---|---|---|---|
| Initial | 0.28 | ND | ND | 0.28 |
| After 3 days at RT | 0.26 | ND | 0.2 | 0.46 |
| After 7 days at RT | 0.32 | 0.21 | 0.36 | 0.89 |

TABLE 4

Amount of the active ingredient (BP) (volume %) maintained in the pharmaceutical compositions after different time periods

| Pharmaceutical composition | 1 | 2 | 3 | 4 | 5 | 6 | Comparative 1 |
|---|---|---|---|---|---|---|---|
| Initial | 99.68 | 99.75 | 99.89 | 99.91 | 99.22 | 99.25 | 99.72 |
| After 3 days at RT | 99.34 | 98.03 | 99.68 | 99.78 | 98.73 | 98.77 | 99.54 |
| After 7 days at RT | 98.40 | 98.53 | 99.32 | 99.58 | 98.30 | 98.48 | 99.11 |

As shown in Table 2, the pharmaceutical compositions of the present invention can be stored at room temperature for at least 3 days without separating into two layers, and some of the pharmaceutical compositions can be stored at room temperature for 7 days (Examples 2 to 4) without separating into two layers. As shown in Table 4, the maintenance of n-butylidenephthalide in the pharmaceutical compositions of the present invention is excellent because the variation of the amount of n-butylidenephthalide is very small even after a long-term storage at room temperature.

The above results prove that the stability of the pharmaceutical composition of the present invention is excellent, and the active ingredient is stable in the medium system. In the pharmaceutical compositions 1, 5 and 6, the amounts of the active ingredient (BP) are about 1000 mg per 1 mL of the medium system.

2. Physical Property Analysis of Pharmaceutical Compositions 2.1 Analytical Method 2.1.1 Droplet Size, Electrical Conductivity and Zeta Potential Analyses The pharmaceutical composition was formulated to provide a sample in which the concentration of n-butylidenephthalide is 200 μg/mL. The droplet size, electrical conductivity and zeta potential of the sample were analyzed using a high concentration nano-droplet size and zeta potential meter (Malvern Nano-ZS ZEN-3600).

2.1.2 Viscosity Analysis

The viscosity analysis was performed by measuring the relationship of viscosity of a sample to shear rate and rheological property of the sample using AR2000 rheometer (stress control) (from TA Instruments; measuring mold: cone and plate; amount of sample: 1 mL). If the viscosity does not change with the shear rate, the sample is a Newtonian fluid; and if the viscosity changed with the shear rate, the sample is a non-Newtonian fluid.

2.1.3 Microstructure Analysis

The pharmaceutical composition was diluted with pure water to 500 times its original volume to provide a sample. The microstructure of the sample was observed using an inverted microscope (IM), a field emission electron scanning microscope (FE-SEM) and a transmission electron microscope (TEM).

2.2 Preparation of Pharmaceutical Compositions

Examples 7-11

The preparation procedures of Example 1 were repeated to prepare pharmaceutical compositions 7 to 11, except that the amounts of the components were adjusted as shown in Table 5. The concentrations of n-butylidenephthalide in the pharmaceutical compositions 7 to 11 are respectively 105 mg per 1 mL of the medium system (the pharmaceutical composition 7), 156 mg per 1 mL of the medium system (the pharmaceutical composition 8), 208 mg per 1 mL of the medium system (the pharmaceutical composition 9), 163 mg per 1 mL of the medium system (the pharmaceutical composition 10) and 111 mg per 1 mL of the medium system (the pharmaceutical composition 11).

TABLE 5

Proportions (volume %) of the components of pharmaceutical compositions

| Pharmaceutical Composition | | 1 | 5 | 6 | 7 | 8 | 9 | 10 | 11 | Comparative 1 |
|---|---|---|---|---|---|---|---|---|---|---|
| Active ingredient | BP | 50 | 50 | 50 | 9.5 | 13.5 | 17.2 | 14 | 10 | 50 |
| First ingredient | PBS | 30 | 30.5 | 30.5 | 60.2 | 43 | 27.6 | 30 | 60 | 30 |
| Second ingredient | K-EL | 10 | 6.5 | 6.5 | 15.1 | 21.6 | 27.6 | 28.7 | 15 | |
| Third ingredient | PEG | 10 | 6.5 | 6.5 | | | | | | 10 |
| | DMSO | | 6.5 | | | | | 27.3 | 15 | |
| | HS 15 | | | | | | | | | 10 |
| | Ethanol | | | 6.5 | 11.4 | 16.4 | 20.6 | | | |
| | PPG | | | | 3.8 | 5.5 | 7 | | | |

2.3 Analytical Results 2.3.1 Analytical Results of Droplet Size, Electrical Conductivity and Zeta Potential The electrical conductivity, zeta potential and average size of the emulsified droplets of pure n-butylidenephthalide, the pharmaceutical compositions 1 and 5 to 11 and the comparative pharmaceutical composition 1 were measured using the analytical method as described in point 2.1.1. The results were tabulated in Table 6. As shown in Table 6, the n-butylidenephthalide droplets contained in the pharmaceutical composition of the present invention is a droplets having a size in the range of 29.89 nm to 1.22 nm, zeta potential was in the range of −6.80 mV to −1.55 mV, and the conductivity was in the range of 12.1 mS/cm to 14.1 mS/cm. This indicated that the pharmaceutical composition of the present invention was oil in water (O/W) type.

TABLE 6

| Formulation | Size (nm) | Zeta potential (mV) | Electrical conductivity (mS/cm) |
|---|---|---|---|
| Pure BP | — | 0.38 | 0.02 |
| Pharmaceutical composition 1 | 1223.21 | −4.41 | 12.5 |
| Pharmaceutical composition 5 | 518.70 | −5.65 | 12.7 |
| Pharmaceutical composition 6 | 320.75 | −6.60 | 12.7 |
| Pharmaceutical composition 7 | 80.05 | −3.65 | 14.1 |
| Pharmaceutical composition 8 | 112.78 | −2.41 | 12.3 |
| Pharmaceutical composition 9 | 29.89 | −2.52 | 12.1 |
| Pharmaceutical composition 10 | 143.79 | −1.55 | 12.7 |
| Pharmaceutical composition 11 | 96.28 | −2.02 | 12.7 |
| Comparative pharmaceutical composition 1 | 318.31 | −6.80 | 12.6 |

2.3.2 Analytical Results of Viscosity

The viscosities of the emulsified droplets of pure n-butylidenephthalide, the pharmaceutical compositions 1 and 5 to 11 and the comparative pharmaceutical composition 1 were measured using the analytical method as described in point 2.1.2, and the average viscosities were calculated accordingly. The results were tabulated in Table 7. As shown in Table 7, pure n-butylidenephthalide and the pharmaceutical compositions are all Newtonian fluids because their viscosities decreased with the shear rate. In addition, the viscosities of the pharmaceutical compositions were in the range of $0.62 \times 10^{-2}$ Pa·s to $10.89 \times 10^{-2}$ Pa·s.

TABLE 7

| Formulation | Average viscosity ($\times 10^{-2}$ Pa · s) ± SD |
|---|---|
| Pure BP | 1.57 ± 0.01 |
| Pharmaceutical composition 1 | 10.89 ± 0.59 |
| Pharmaceutical composition 5 | 6.96 ± 0.69 |
| Pharmaceutical composition 6 | 4.56 ± 0.37 |
| Pharmaceutical composition 7 | 0.99 ± 0.02 |
| Pharmaceutical composition 8 | 8.69 ± 0.13 |
| Pharmaceutical composition 9 | 9.58 ± 0.23 |
| Pharmaceutical composition 10 | 1.99 ± 0.06 |
| Pharmaceutical composition 11 | 0.62 ± 0.02 |
| Comparative pharmaceutical composition 1 | 4.49 ± 0.30 |

2.3.3 Analytical Results of Microstructure

Figure 1B:
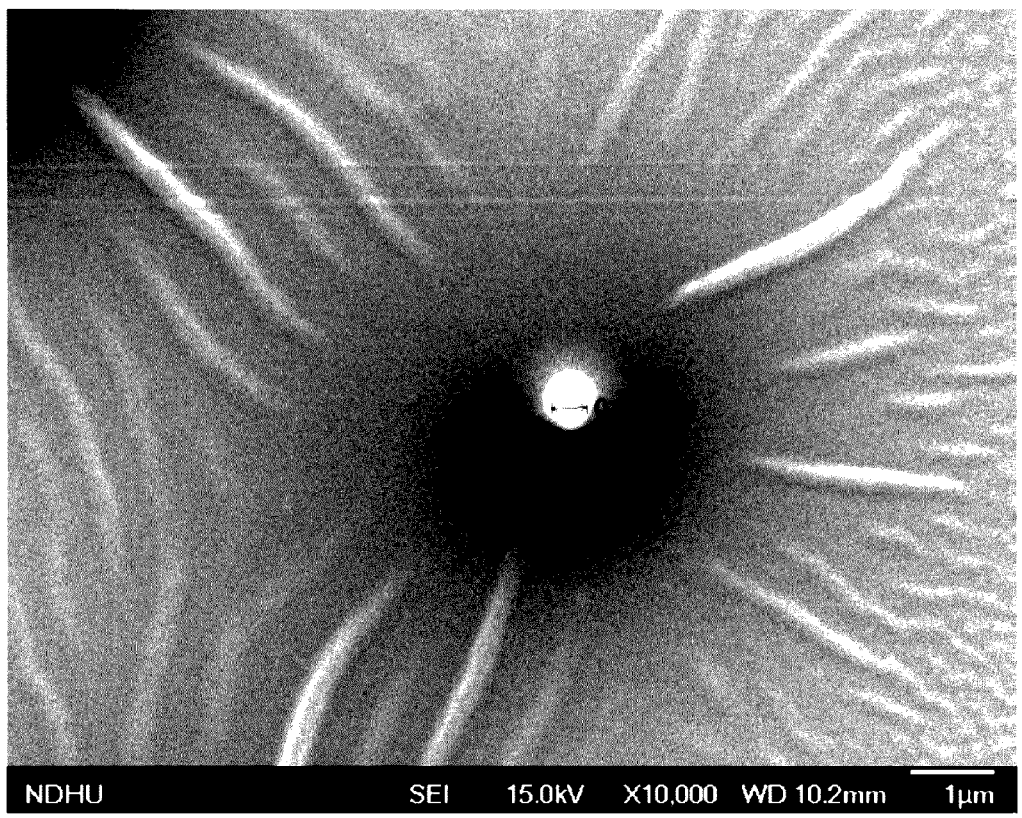
FIG. 1B shows the field emission electron scanning microscope (FE-SEM) image (10000×; bar: 1 μm) of an embodiment of the pharmaceutical composition according to the present invention.
Figure 1C:
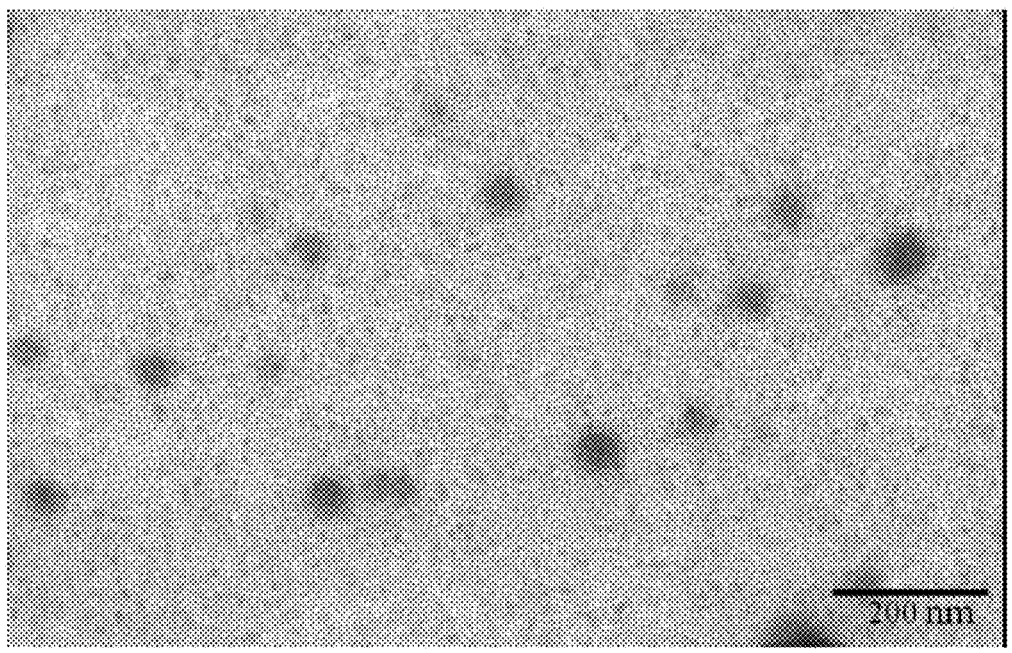
FIG. 1C shows the transmission electron microscope (TEM) image (80000×; bar: 200 nm) of an embodiment of the pharmaceutical composition according to the present invention.

The microstructure of the pharmaceutical composition 5 was measured using the analytical method as described in point 2.1.3. The result was shown in FIG. 1A, FIG. 1B and FIG. 1C, wherein FIG. 1A is the inverted microscope (IM) image (400×; bar: 50 μm) of pharmaceutical composition 5, FIG. 1B is the field emission electron scanning microscope (FE-SEM) image (10000×; bar: 1 μm) of pharmaceutical composition 5, and FIG. 1C is the transmission electron microscope (TEM) image (80000×; bar: 200 nm) of pharmaceutical composition 5. As can be seen from FIG. 1A to FIG. 1C, the droplets of n-butylidenephthalide in the pharmaceutical composition of the present invention were in nanometric to micrometric range and had a nearly spherical morphology.

3. In Vitro Experiments of Pharmaceutical Compositions 3.1. Analytical Objects

Experimental group: pharmaceutical composition 1, pharmaceutical composition 5 and pharmaceutical composition 6; and Control group: comparative pharmaceutical composition 1.

3.2 Analytical Methods 3.2.1 Low-Temperature Stability Test

The pharmaceutical compositions were stored at 4° C. for 30 days and photographed and observed whether the appearances of the pharmaceutical compositions have separating layers or not. The appearances of the pharmaceutical compositions before and after the storage were compared.

3.2.2 Cytotoxicity Test ($IC_{50}$ Value)

GBM 8401 cells (i.e., a human brain glioblastoma multiforme cell line) were cultured in a 96-well culture plate with a cell number of $6 \times 10^3$ per well, and treated with pure n-butylidenephthalide (BP) or one of the pharmaceutical compositions for 24 hours. The treatment concentrations of active ingredient, n-butylidenephthalide (BP), were 0 μg/mL (i.e., control group), 12.5 μg/mL, 25 μg/mL, 50 μg/mL, 100 μg/mL and 200 μg/mL, respectively. Then, the half maximal inhibitory concentration ($IC_{50}$) of each pharmaceutical composition to GBM 8401 cells was analyzed by MTT (3-(4,5-cimethylthiazol-2-yl)-2,5-diphenyl tetrazolium bromide) cell survival assay, to evaluate the cytotoxic effect.

3.2.3 Cytotoxic Stability Test

Pharmaceutical composition 5 was separated into five batches, and the batches were stored for 0, 7, 14, 30 and 60 days, respectively. GBM 8401 cells were cultured in a 96-well culture plate with a cell number of $6 \times 10^3$ per well, and treated with one of the stored batches of pharmaceutical composition 5 for 24 hours. Then, the half maximal inhibitory concentration ($IC_{50}$) of each of the stored batches of pharmaceutical composition 5 to GBM 8401 cells was analyzed by MTT cell survival assay, to evaluate the influence of the storage period on the cytotoxic effect of the pharmaceutical composition. The treatment concentrations of the active ingredient, n-butylidenephthalide (BP), were 0 μg/mL (i.e., control group), 12.5 μg/mL, 25 μg/mL, 50 μg/mL, 100 μg/mL and 200 μg/mL, respectively.

3.2.4 In Vitro Artificial Cellulose Membrane Test

Figure 5:
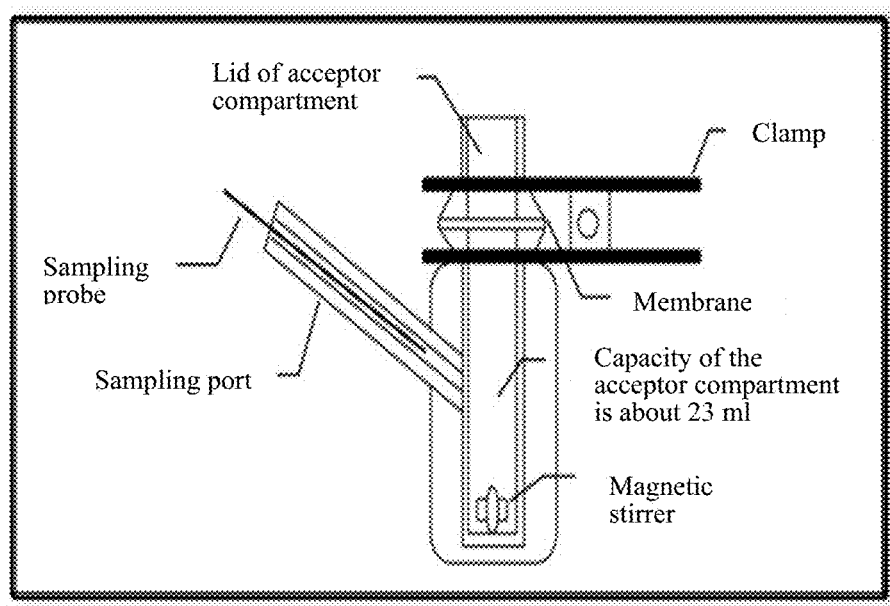
FIG. 5 is a schematic drawing of the Franz diffusion device.
Figure 6:
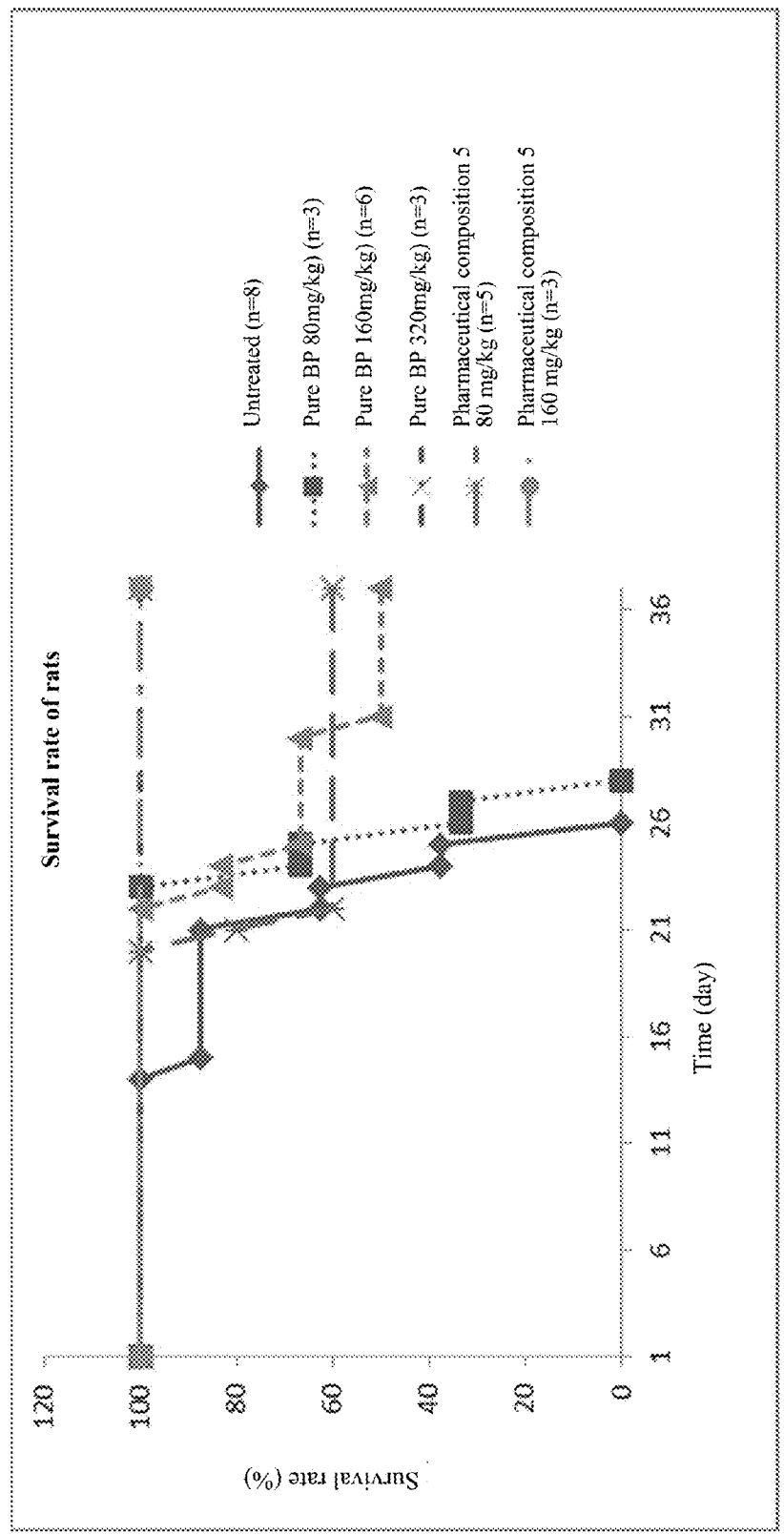
FIG. 6 is a statistical chart showing the survival rate of rats after being treated with different medical treatments.

A Franz diffusion device (SUNMEI instruments Co., Ltd, Taiwan) shown in FIG. 5 was used to estimate the ability of pure n-butylidenephthalide (BP) liquid and the pharmaceutical compositions to permeate trough the artificial cellulose membrane, to simulate their permeation through a nasal mucosa. The superficial area of diffusion of the device is about 4.5 cm², and the capacity volume of receptor chamber of the device is about 23 mL.

The specific testing method includes: (i) cutting the artificial cellulose membrane into appropriate size and placing the cut membrane into Hepes (4-(2-hydroxyethyl)-1-piperazineethanesulfonic acid) buffer (118 mM NaCl+1.2 mM MgSO₄+4.8 mM KCl+5.5 mM D-glucose+2.5 mM CaCl₂+20 mM Hepes) to soak for 10 minutes; (ii) adding 2 mL of pure n-butylidenephthalide (BP) liquid or 2 mL of pharmaceutical composition (3 mg/mL) into the donor chamber; (iii) adding the Hepes buffer into the receptor chamber and stirring the mixture by a magnetic stirring method (speed: 300 rpm); (iv) conducting the test at 37° C., sampling 1 mL of sample from the sampling probe of the receptor chamber every 1 hour (10 hours in total), and resupplying 1 mL of pre-warmed Hepes buffer into the receptor chamber at the same time; (v) measuring the absorption spectrum of the sampled solution by a spectrophotometer at a wavelength of 310 nm, and calculating the concentration of n-butylidenephthalide; and (vi) calculating the permeability coefficient ($P_{eff}$) and flux (J) by using the following Formula 1 and Formula 2, respectively.

$$P_{eff} = \frac{V}{AC0}\frac{dc}{dt} = \frac{V}{AC0}\frac{dc}{dt} \quad \text{(Karasulu et al., 2008)} \quad \text{Formula 1}$$

$$J == \left(\frac{dc}{dt}\right)\frac{V}{A} = \left(\frac{dc}{dt}\right)\frac{V}{A} \quad \text{Formula 2}$$

V: Capacity of receptor chamber (mL)
$C_0$: Initial supplied concentration of drug (μg/mL)
$P_{eff}$: Permeability coefficient (cm/s)
J: Flux (μg/cm²·s)
A: Superficial area of diffusion (cm²)

$$\left(\frac{dc}{dt}\right):$$

Change of the concentration along with time under a stable status (μg/mLs)

3.2.5 In Vitro Cell Line Permeation Test

RPMI 2650 cells (i.e., a human nasal septum squamous cell line) were seeded in a collagen-coated cell insert with 0.4 μm pore size and cultured for 2 days to lead the cells to form a cellular monolayer on the insert. The cell insert was then transferred into a 12-well plate with 1.5 mL of Hepes buffer inside. 0.5 mL of Hepes buffer containing pure n-butylidenephthalide or the pharmaceutical composition was added into the 12-well plate. Next, the 12-well plate was placed into an incubator (37° C., 5% $CO_2$) and incubated. The buffer in each well of the 12-well plate was collected every 1 hour (6 hours in total), and the absorption spectrum of the sampled buffer was detected by a spectrophotometer at −310 nm wavelength to calculate the concentration of n-butylidenephthalide or the pharmaceutical composition. The permeability coefficient ($P_{eff}$) and flux (J) were calculated by using the above Formula 1 and Formula 2.

3.3 Results of the Test 3.3.1 Results of the Low-Temperature Stability Test

Figure 2A:
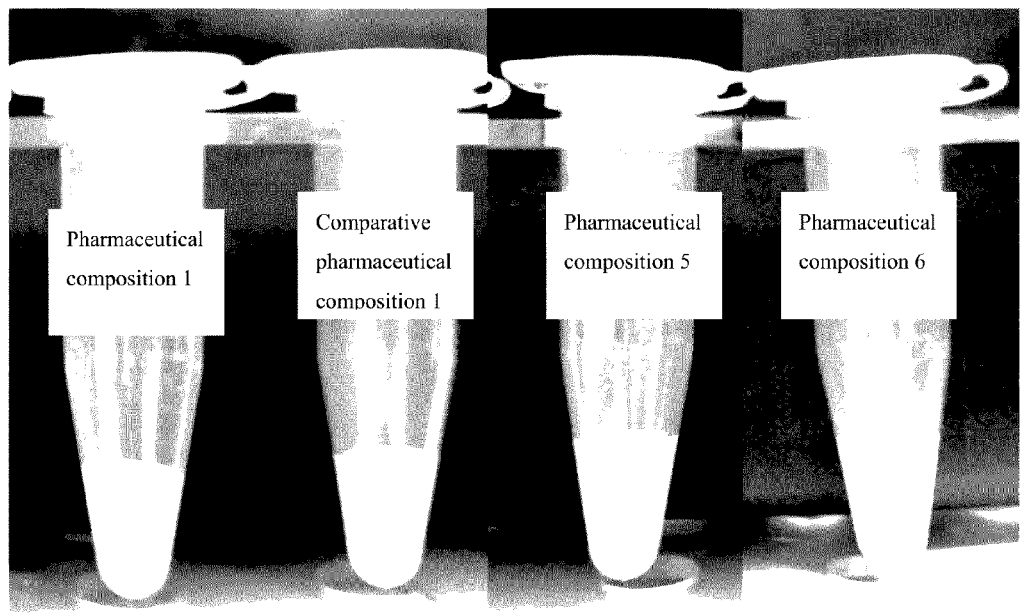
FIG. 2A is a picture showing the appearance of the pharmaceutical compositions according to the present invention and the comparative pharmaceutical composition before a long-term storage at 4° C.
Figure 2B:
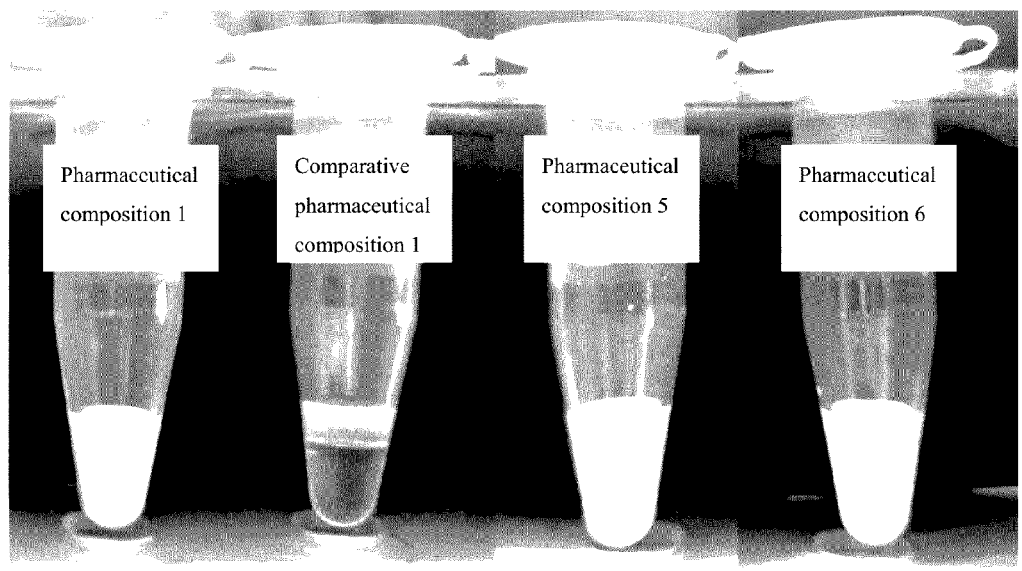
FIG. 2B is a picture showing the appearance of the pharmaceutical compositions according to the present invention and the comparative pharmaceutical composition after a long-term storage at 4° C.

The stability of pharmaceutical composition 1, comparative pharmaceutical composition 1, pharmaceutical composition 5 and pharmaceutical composition 6 at low temperature was examined by the method as described in point 3.2.1. The results were shown in FIG. 2A and FIG. 2B, wherein FIG. 2A was taken before the storage and FIG. 2B was taken after the storage. As shown in FIG. 2A and FIG. 2B, the appearances of pharmaceutical compositions of the present invention (pharmaceutical compositions 1, 5 and 6) before and after the storage remained the same, and the pharmaceutical compositions remained homogeneous and did not separate into layers, while the comparative pharmaceutical composition 1 separated into layers after the storage. This indicates that the pharmaceutical composition of the present invention has an excellent stability at low temperature.

Figure 3:
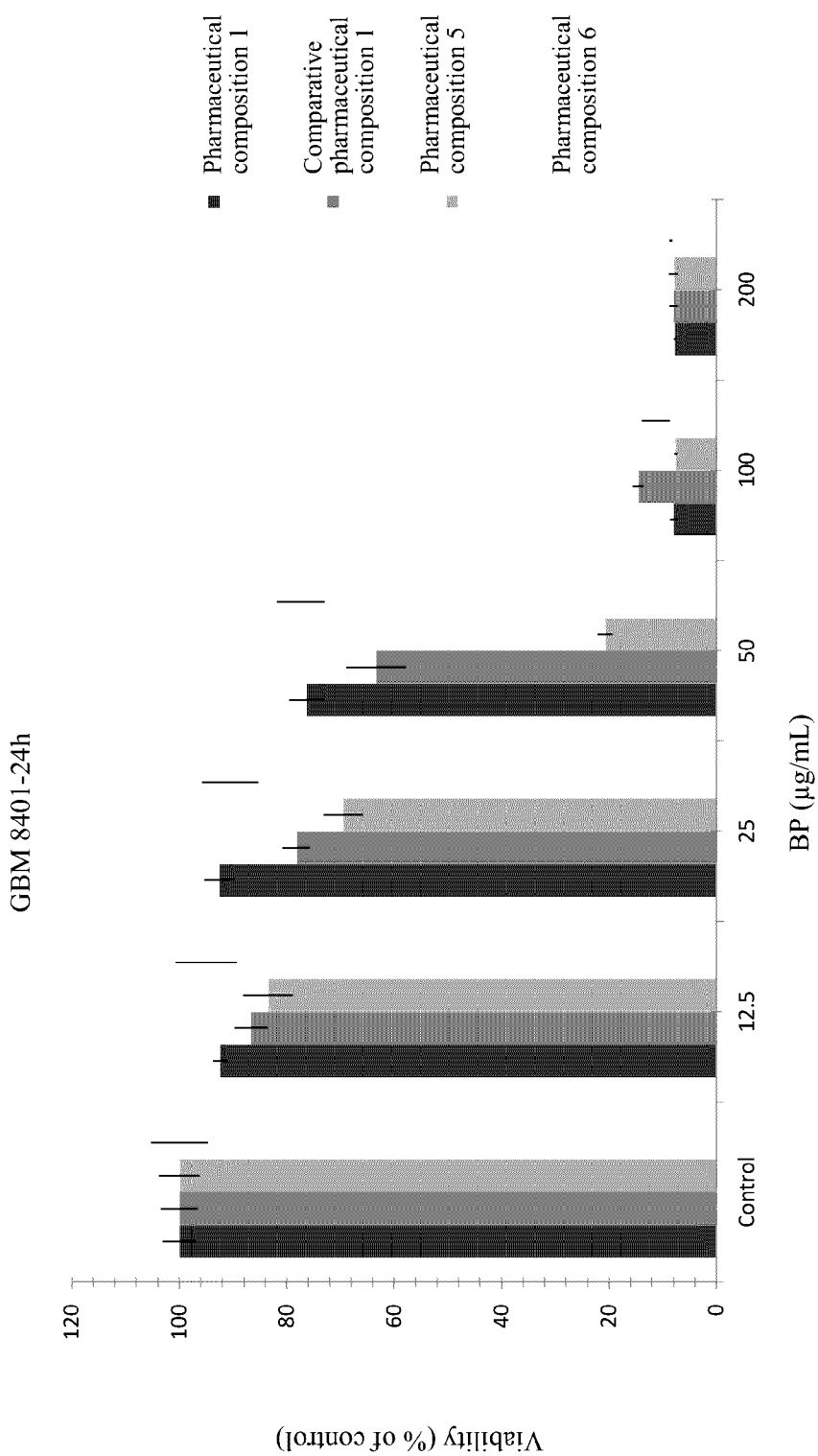
FIG. 3 is a statistical chart showing the activity of the pharmaceutical compositions according to the present invention (with different medium systems) and the comparative pharmaceutical composition, wherein the vertical axis shows the viability of GBM8401 cells (i.e., human malignant tumor cell lines), expressed as a percentage relative to the control group where the cells are not treated with n-butylidenephthalide, and the lateral axis shows the concentration of the active ingredient, "n-butylidenephthalide"

3.3.2 Results of Cytotoxicity Test:

the cytotoxicity test of pure n-butylidenephthalide, pharmaceutical composition 1, comparative pharmaceutical composition 1, pharmaceutical composition 5 and pharmaceutical composition 6 was conducted by the method as described in point 3.2.2. The results were shown in FIG. 3 and Table 8. As shown in FIG. 3, as compared to the "control group," the survival rate of GBM 8401 cells was decreased along with the increment in the dosage of the active ingredient, n-butylidenephthalide (BP). In addition, among the pharmaceutical compositions, pharmaceutical composition 5 has the best cytotoxic effect, the $IC_{50}$ of pharmaceutical composition 5 to cell survival is 28.20 μg/mL.

TABLE 8

| Formulation | $IC_{50}$ (μg/mL) |
|---|---|
| Pure BP | 70 |
| Pharmaceutical composition 1 | 106.35 |
| Pharmaceutical composition 5 | 28.20 |
| Pharmaceutical composition 6 | 88.62 |
| Comparative pharmaceutical composition 1 | 62.22 |

3.3.3 Results of Cytotoxic Stability Test

Figure 4:
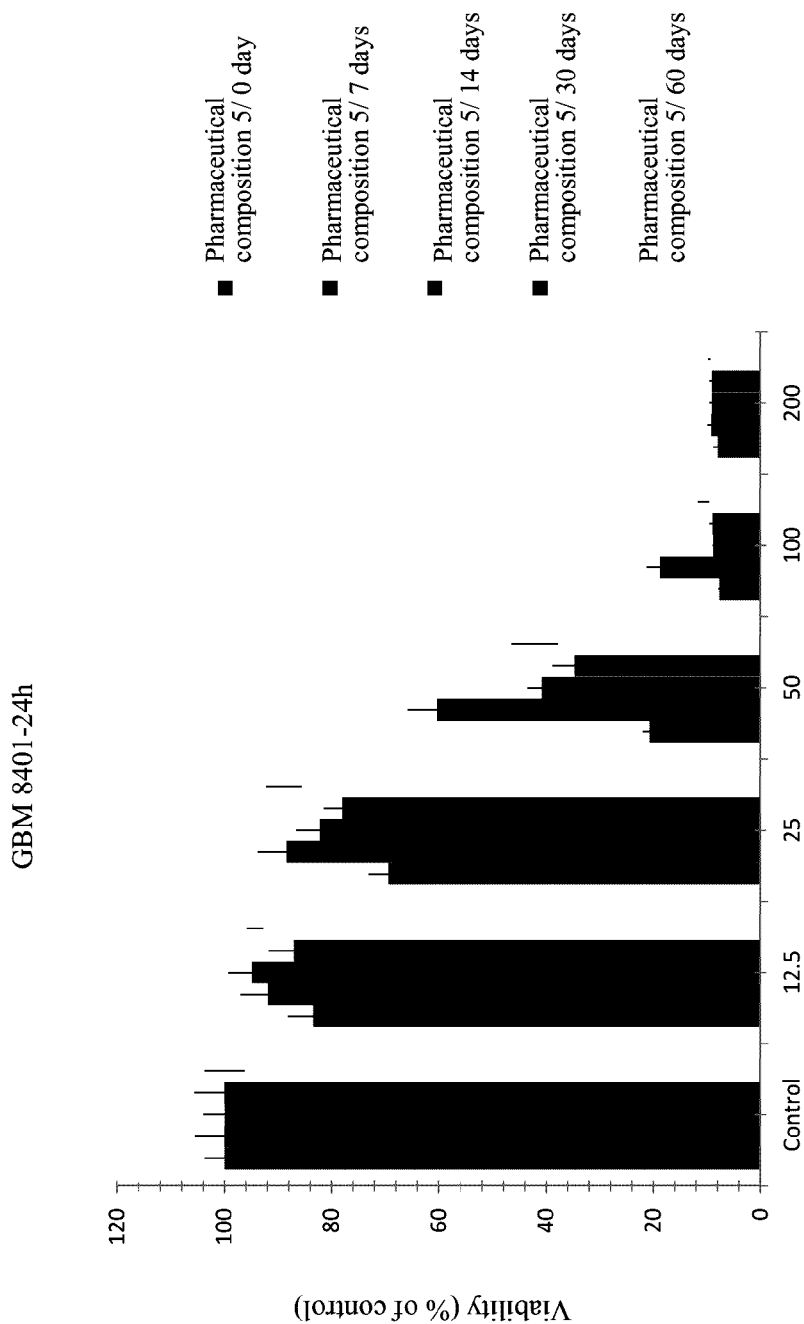
FIG. 4 is a statistical chart showing the effect of storage time on the activity of the pharmaceutical composition according to the present invention, wherein the vertical axis shows the viability of GBM8401 cells, expressed as a percentage relative to the control group where the cells are not treated with n-butylidenephthalide, and the lateral axis shows the concentration of n-butylidenephthalide.

The cytotoxic stability test of pharmaceutical composition 5 was conducted by the method as described in point 3.2.3. The results are shown in FIG. 4. As shown in FIG. 4, as compared to the "control group," no matter how long the storage period is, the survival rate of treated GBM 8401 cells in each group was maintained with the regular that the survival rate was reduced along with the increment in the dosage of the active ingredient, n-butylidenephthalide. The aforementioned results indicate that the cytotoxic effect of pharmaceutical composition 5 on the brain glioblastoma multiforme cells would not be influenced by the storage period and thus is a stable formulation.

3.3.4 Results of In Vitro Artificial Cellulose Membrane Test

In vitro artificial cellulose membrane test of pure n-butylidenephthalide, pharmaceutical composition 1, comparative pharmaceutical composition 1, pharmaceutical composition 5 and pharmaceutical composition 6 was conducted by the method as described in point 3.2.4. The results were shown in the following Table 9. As shown in Table 9, pharmaceutical composition 5 and pharmaceutical composition 6 have the highest permeability coefficient ($P_{eff}$), while pure n-butylidenephthalide has the lowest permeability coefficient. The aforementioned results indicate that, the permeation ability of the pharmaceutical composition of the present invention is significantly better than that of pure n-butylidenephthalide, and pharmaceutical composition 5 and pharmaceutical composition 6 has the best permeation ability.

TABLE 9

| Formulation | Flux ($10^{-3}$ µg/cm$^2$·s) ± SD | Coefficient of determination ($r^2$) ± SD | $P_{eff}$ ($10^{-6}$ cm/s) ± SD |
|---|---|---|---|
| Pure BP | 2.29 ± 0.23 | 0.97 ± 0.02 | 0.76 ± 0.08 |
| Pharmaceutical composition 1 | 2.71 ± 0.25 | 0.85 ± 0.04 | 0.98 ± ± 0.14 |
| Pharmaceutical composition 5 | 11.60 ± 0.19 | 0.96 ± 0.02 | 3.85 ± 0.06 |
| Pharmaceutical composition 6 | 11.60 ± 0.88 | 0.97 ± 0.01 | 3.85 ± 0.29 |
| Comparative pharmaceutical composition 1 | 11.20 ± 0.42 | 0.92 ± 0.06 | 3.57 ± 0.30 |

3.3.5 Results of In Vitro Cell Line Permeation Test

In vitro cell line permeation test of pure n-butylidenephthalide, pharmaceutical composition 1, comparative pharmaceutical composition 1, pharmaceutical composition 5 and pharmaceutical composition 6 was conducted by the method as described in point 3.2.5. The results are shown in the following Table 10. As shown in Table 10, the permeability coefficient ($P_{eff}$) of pharmaceutical composition 5 is the highest, while the permeability coefficient of pure n-butylidenephthalide liquid is the lowest. The aforementioned results indicate that, the ability of pharmaceutical composition of the present invention to permeate through cells is significantly better than that of pure n-butylidenephthalide, and the ability of pharmaceutical composition 5 to permeate through cells is the best.

TABLE 10

| Formulation | Flux ($10^{-3}$ µg/cm$^2$·s) ± SD | Coefficient of determination ($r^2$) ± SD | $P_{eff}$ ($10^{-6}$ cm/s) ± SD |
|---|---|---|---|
| Pure BP | 0.32 ± 0.02 | 0.99 ± 0.01 | 1.59 ± 0.09 |
| Pharmaceutical composition 1 | 0.92 ± 0.05 | 0.99 ± 0.00 | 4.60 ± 0.24 |
| Pharmaceutical composition 5 | 1.63 ± 0.37 | 0.95 ± 0.02 | 8.16 ± 1.85 |
| Pharmaceutical composition 6 | 1.46 ± 0.87 | 0.97 ± 0.04 | 7.32 ± 4.32 |
| Comparative pharmaceutical composition 1 | 1.42 ± 1.38 | 0.98 ± 0.01 | 5.96 ± 8.40 |

4. Animal Experiments of the Pharmaceutical Compositions 4.1. Analytical Methods 9 L (i.e., a rat brain gliosarcoma cell line) tumor tissue was intracranially transplanted into rats. The test of drug treatment was conducted after the intracranial tumor formed. The test method includes: (i) using 400 mg/kg of chloral hydrate (Sigma-Aldrich Company Ltd.) to anesthetize the rats, shaving the hair on the head of rats after the rats were in a coma, and fixing the rats in a stereotaxic instrument (Lab Standard™ Stereotaxic Instrument); (ii) scissoring the scalp by shears to expose the cranium, setting the bregma as a center, and drilling a 5 mm hole at the positioned drilling site 3 mm right to and 5 mm below the bregma on the cranium by a drill; (iii) clamping the prepared 9 L tumor tissue (1×1×1 mm$^3$) by a forceps and transplanting it into 3 mm depths within the brain, and then, resting for 1 minute to coagulate the blood, removing the forceps, and coating the bone wax on the hole, lastly, suturing the scalp of rats and administering the rats with antibiotics; (iv) 7 days after the transplantation of tumor tissue, randomly grouping the rats as the following Table 11, and then, sucking a drug (n-butylidenephthalide (BP) or pharmaceutical composition 5) by a pipette and dropping the drug into the nasal cavity of the rats to conduct an intranasal administration, and repeating the administration for 30 days and recording the body weight of rats and the number of dead rats during this medical treatment; and (v) removing the tumor, and then, measuring the length-breadth of tumor by an electronic vernier caliper and calculating the total volume of tumor by using the following Formula 3, measuring the weight of tumor at the same time, and drawing the obtained values into a bar diagram and a curve diagram, to determine the therapeutic effect.

TABLE 11

| Groups | Treatment methods |
|---|---|
| Control group | Rats intracranially transplanted with 9 L tumor tissue, but without drug treatment (*n = 8) |
| Negative control group | Rats intranasally administrated with original n-butylidenephthalide (BP) liquid (80 mg/kg) (n = 3) |
|  | Rats intranasally administrated with original n-butylidenephthalide (BP) liquid (160 mg/kg) (n = 6) |
|  | Rats intranasally administrated with original n-butylidenephthalide (BP) liquid (320 mg/kg) (n = 3) |
| Experimental group | Rats intranasally administrated with pharmaceutical composition 5 (80 mg/kg) (n = 5) |
|  | Rats intranasally administrated with pharmaceutical composition 5 (160 mg/kg) (n = 3) |

*"n" is the number of rats in each group $$\text{Volume of tumor (mm}^3\text{)} = \frac{\text{length} \times \text{breadth}^2}{2} \qquad \text{Formula 3}$$

4.2 Results of Animal Experiments

The animal experiments were conducted by the method as described in point 4.1. The results are shown in FIG. 6 and FIG. 7A to FIG. 7C. As shown in FIG. 6 and FIG. 7A to FIG. 7C, as compared to the "control group," pure n-butylidenephthalide (BP) in a concentration of 160 mg/kg or 320 mg/kg is effective in inhibiting the growth of tumor. The aforementioned result indicates that the intranasal administration of pure n-butylidenephthalide can actually provide an effect of treating malignant tumor.

As shown in FIG. 6 and FIG. 7A to 7C, 30 days after the intranasal administrations of pure n-butylidenephthalide (160 mg/kg) and pharmaceutical composition 5 (80 mg/kg), the rats in these groups have significantly increased and similar survival rates and significantly reduced and similar volume and weight of tumor. This indicates that, the pharmaceutical composition of the present invention can achieve the same therapeutic effect as pure n-butylidenephthalide with a lower effective amount of n-butylidenephthalide (BP) which is merely half of that in the pure n-butylidenephthalide case.

Figure 7A:
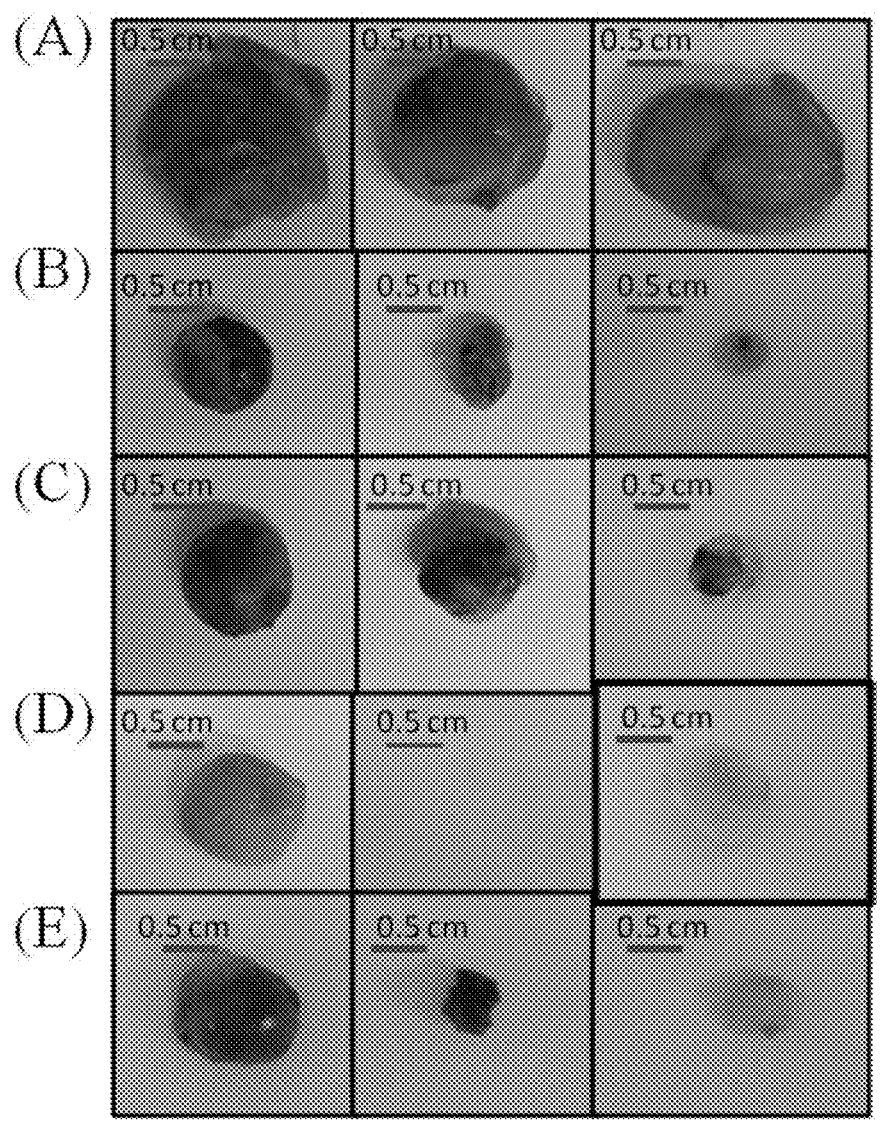
FIG. 7A is a picture showing the growth of tumors intracranially transplanted into rats after the rats were treated with different medical treatments, wherein the pictures were taken when the rats died or on Day 37 of the medical treatments.
Figure 7B:
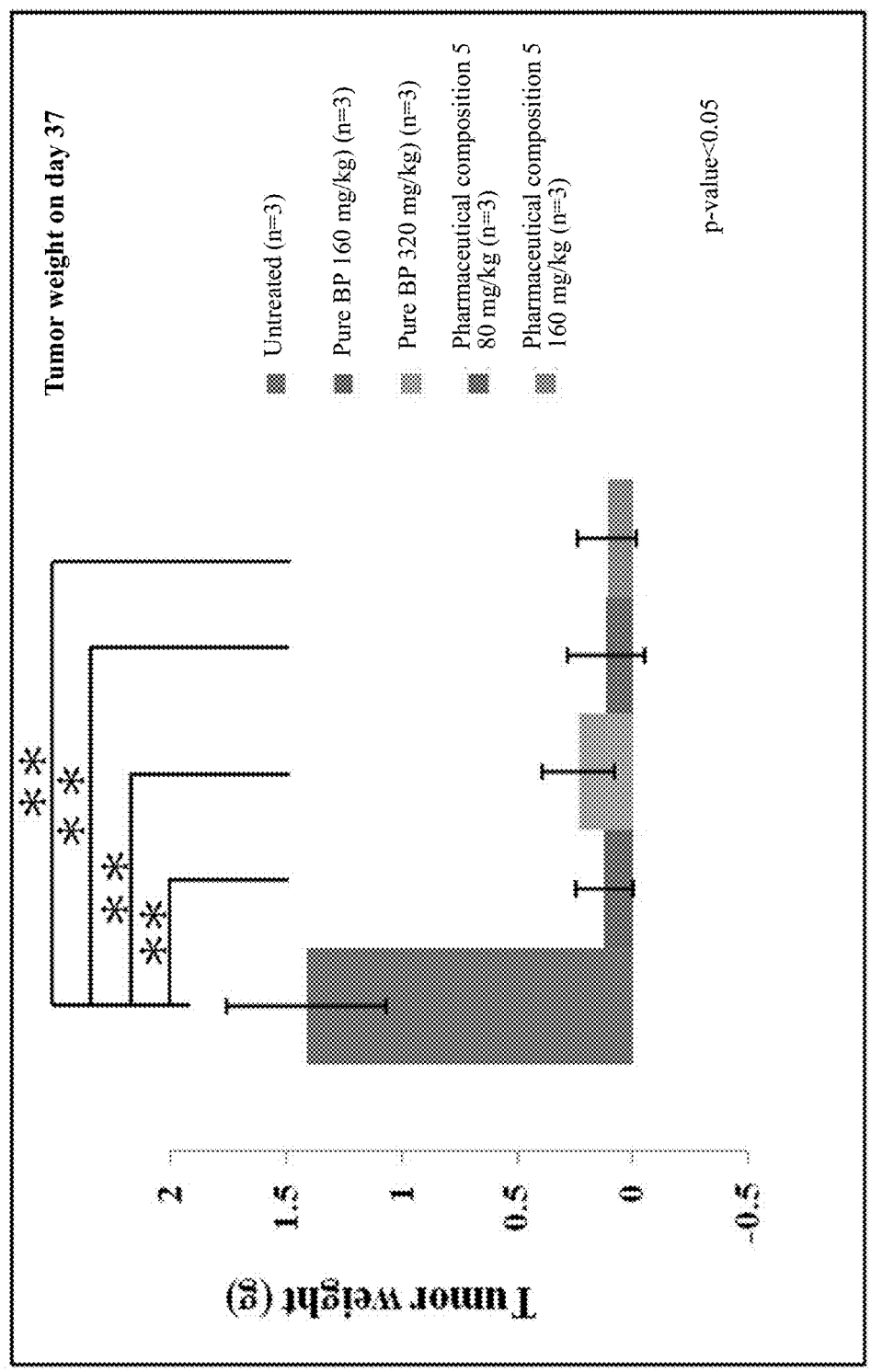
FIG. 7B is a statistical chart showing the weight of tumors intracranially transplanted into rats after the rats were treated with different medical treatments, wherein the pictures were taken when the rats died or on Day 37 of the medical treatments.
Figure 7C:
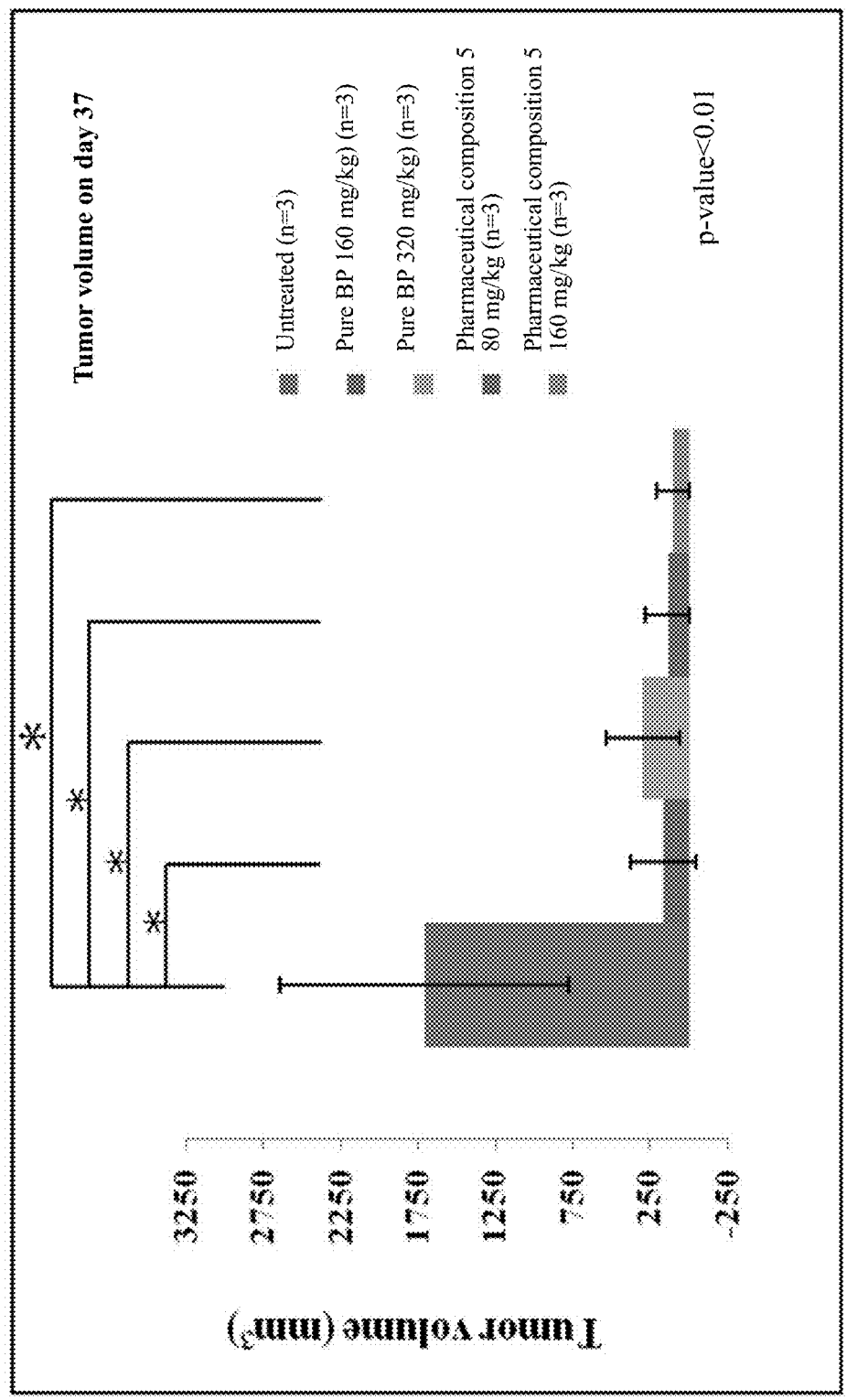
FIG. 7C is a statistical chart showing the volume of tumors intracranially transplanted into rats after the rats were treated with different medical treatments, wherein the pictures were taken when the rats died or on Day 37 of the medical treatments.

As shown in FIG. 7B and FIG. 7C, 30 days after the administration of pharmaceutical composition 5 (160 mg/kg), the weight of tumor was reduced by about 92% (FIG. 7B), and the volume of tumor was reduced by about 94% (FIG. 7C). The results indicates the pharmaceutical composition 5 (160 mg/kg) of the present invention is excellently effective in treating malignant tumor.

The above in vitro and animal experiments all indicate that, in virtue of manufacturing n-butylidenephthalide (BP) into a pharmaceutical composition of the present invention, the efficiency of active ingredients to permeate through the nasal mucosa after intranasal administration can be increased, and the therapeutic effect, especially the effect of treating malignant tumor, is synergistic.

The above disclosure is related to the detailed technical contents and inventive features thereof. People skilled in this field may proceed with a variety of modifications and replacements based on the disclosures and suggestions of the present invention as described without departing from the characteristics thereof. Nevertheless, although such modifications and replacements are not fully disclosed in the above descriptions, they have substantially been covered in the following claims as appended.

What is claimed is:

1. A stable pharmaceutical composition comprising:
   (a) a medium system, comprising a first ingredient, a second ingredient and a third ingredient, wherein the first ingredient is a phosphate buffered saline, the second ingredient is selected from the group consisting of vegetable oils, animal oils, fatty acids and combinations thereof, and the third ingredient is selected from the group consisting of polyethylene glycol, dimethyl sulfoxide (DMSO), ethanol, polypropylene glycol, polysorbate, polyoxyethylated vegetable oil, ethyl acetate, 2-hydroxyethyl 12-hydroxyoctadecanoate, tocopheryl polyethylene glycol succinate and combinations thereof; and
   (b) n-butylidenephthalide (BP),
   wherein among the medium system, the volume ratio of the first ingredient to the second ingredient is from 1:2 to 20:1, and the volume ratio of the first ingredient to the third ingredient is from 1:2 to 30:1.

2. The composition as claimed in claim 1, wherein the vegetable oil is selected from the group consisting of canola oil, coconut oil, corn oil, cotton seed oil, olive oil, palm oil, peanut oil, rape seed oil, safflower seed oil, sesame oil, bean oil, heliotrope oil, almond oil, cashewnut oil, hazelnut oil, walnut oil, hickory nut oil, pine nut oil, pistachio oil, castor oil and combinations thereof; and the animal oil is selected from the group consisting of fish oil, fish liver oil, lard oil, tallow oil, caproin, chicken oil, duck oil and combinations thereof.

3. The composition as claimed in claim 1, wherein the second ingredient is a modified castor oil.

4. The composition as claimed in claim 3, wherein the modified castor oil is polyethoxylated castor oil; and the third ingredient is selected from the group consisting of polyethylene glycol, dimethyl sulfoxide, ethanol, polypropylene glycol and combinations thereof.

5. The composition as claimed in claim 4, wherein the third ingredient is selected from the group consisting of polyethylene glycol, dimethyl sulfoxide, ethanol and combinations thereof.

6. The composition as claimed in claim 5, wherein the third ingredient is a combination of polyethylene glycol and dimethyl sulfoxide or a combination of polyethylene glycol and ethanol.

7. The composition as claimed in claim 6, wherein the third ingredient is a combination of polyethylene glycol and dimethyl sulfoxide.

8. The composition as claimed in claim 1, wherein the BP is in an amount of 0.001 mg to 1500 mg per milliliter (mL) of the medium system.

9. The composition as claimed in claim 2, wherein the BP is in an amount of 0.001 mg to 1500 mg per milliliter (mL) of the medium system.

10. The composition as claimed in claim 3, wherein the BP is in an amount of 0.001 mg to 1500 mg per milliliter (mL) of the medium system.

11. The composition as claimed in claim 4, wherein the BP is in an amount of 0.001 mg to 1500 mg per milliliter (mL) of the medium system.

12. The composition as claimed in claim 5, wherein the BP is in an amount of 0.001 mg to 1500 mg per milliliter (mL) of the medium system.

13. The composition as claimed in claim 7, wherein the BP is in an amount of 0.001 mg to 1500 mg per milliliter (mL) of the medium system.

* * * * *